United States Patent
Chen et al.

(10) Patent No.: US 7,022,342 B2
(45) Date of Patent: Apr. 4, 2006

(54) CONTROLLED RELEASE ORAL DOSAGE FORM OF BETA-ADRENERGIC BLOCKING AGENTS

(75) Inventors: Chih-Ming Chen, Davie, FL (US); Xiu Xiu Cheng, Davie, FL (US)

(73) Assignee: Andrx Corporation, Inc., Davie, FL (US)

( * ) Notice: Subject to any disclaimer, the term of this patent is extended or adjusted under 35 U.S.C. 154(b) by 37 days.

(21) Appl. No.: 10/109,408

(22) Filed: Mar. 28, 2002

(65) Prior Publication Data

US 2003/0185887 A1  Oct. 2, 2003

(51) Int. Cl.
*A61K 9/36* (2006.01)

(52) U.S. Cl. .................. 424/480; 424/464; 424/465; 424/468; 424/472; 424/474

(58) Field of Classification Search .............. 424/453, 424/457, 459, 501, 497, 489, 493, 490
See application file for complete search history.

(56) References Cited

U.S. PATENT DOCUMENTS

| | | |
|---|---|---|
| 3,337,628 A | 8/1967 | Crowther et al. |
| 4,138,475 A | 2/1979 | McAinsh et al. |
| 4,248,856 A | 2/1981 | Guley et al. |
| 4,248,857 A | 2/1981 | DeNeale et al. |
| 4,248,858 A * | 2/1981 | Guley et al. ............. 424/493 |
| 4,309,404 A | 1/1982 | DeNeale et al. |
| 4,309,405 A | 1/1982 | Guley et al. |
| 4,309,406 A | 1/1982 | Guley et al. |
| 4,394,390 A | 7/1983 | Hussain et al. |
| 4,443,428 A | 4/1984 | Oshlack et al. |
| 4,469,690 A | 9/1984 | Ackerman et al. |
| 4,470,987 A | 9/1984 | Wurtman et al. |
| 4,522,804 A | 6/1985 | Dunn |
| 4,600,708 A | 7/1986 | Reuter et al. |
| 4,681,765 A | 7/1987 | Guley |
| 4,711,887 A | 12/1987 | Briggs et al. |
| 4,728,512 A | 3/1988 | Mehta et al. |
| 4,780,318 A | 10/1988 | Appelgren et al. |
| 4,783,444 A | 11/1988 | Watkins et al. |
| 4,792,452 A | 12/1988 | Howard et al. |
| 4,883,660 A | 11/1989 | Blackman et al. |
| 4,888,354 A | 12/1989 | Chang et al. |
| 4,898,737 A | 2/1990 | Panoz et al. |
| 4,906,635 A | 3/1990 | Neustadt et al. |
| 4,931,283 A | 6/1990 | Tsuk |
| 4,933,184 A | 6/1990 | Tsuk |
| 4,952,402 A | 8/1990 | Sparks et al. |
| 4,983,401 A | 1/1991 | Eichel et al. |
| 4,988,736 A | 1/1991 | Foldesy |
| 5,026,559 A | 6/1991 | Eichel et al. |
| 5,095,151 A | 3/1992 | Guley et al. |
| 5,133,974 A * | 7/1992 | Paradissis et al. ........ 424/480 |
| 5,169,638 A | 12/1992 | Dennis et al. |
| 5,242,949 A | 9/1993 | Goldberg et al. |
| 5,268,182 A | 12/1993 | Brinker et al. |
| 5,376,384 A | 12/1994 | Eichel et al. |
| 5,387,613 A | 2/1995 | Goldberg et al. |
| 5,478,573 A | 12/1995 | Eichel et al. |
| 5,498,636 A | 3/1996 | Goldberg et al. |
| 5,525,347 A | 6/1996 | Kellner et al. |

(Continued)

*Primary Examiner*—Thurman K. Page
*Assistant Examiner*—Micah-Paul Young
(74) *Attorney, Agent, or Firm*—Hedman & Costigan, P.C.

(57) ABSTRACT

A sustained release beta-adrenergic receptor blocking agent, preferably propranolol, formulation.

8 Claims, 8 Drawing Sheets

U.S. PATENT DOCUMENTS

| | | |
|---|---|---|
| 5,700,410 A | 12/1997 | Nakamichi et al. |
| 5,773,023 A | 6/1998 | Deckner et al. |
| 5,783,215 A * | 7/1998 | Arwidsson et al. ......... 424/501 |
| 5,830,497 A | 11/1998 | Yamanaka et al. |
| 5,851,555 A | 12/1998 | Sanghvi et al. |
| 5,881,926 A | 3/1999 | Ross |
| 5,919,828 A | 7/1999 | Weglicki |
| 5,932,572 A | 8/1999 | Dean et al. |
| 5,945,125 A | 8/1999 | Kim |
| 5,968,554 A | 10/1999 | Beiman et al. |
| 5,985,317 A | 11/1999 | Venkateshwaran et al. |
| 6,046,177 A * | 4/2000 | Stella et al. ................... 514/58 |
| 6,270,805 B1 * | 8/2001 | Chen et al. ................. 424/497 |

* cited by examiner

CONTROLLED RELEASE ORAL DOSAGE FORM OF BETA-ADRENERGIC BLOCKING AGENTS

BACKGROUND OF THE INVENTION

1. Field of the Invention

The present invention relates to oral controlled release dosage formulations containing a beta-adrenergic blocking agent. More specifically, the present invention relates to an oral dosage formulation in the form of a capsule containing pellets comprising a beta-adrenergic blocking agents, such as propranolol, atenolol, metoprolol, acebutolol, nadolol, sotalol, bisoprolol, penbutolol, timolol, betaxolol, labetalol, pindolol, carteolol, esmolol or their pharmaceutically acceptable derivatives, salts and stereoisomers. Most preferably the beta-adrenergic blocking agent is propranolol hydrochloride.

2. Description of the Prior Art

Beta-adrenergic blocking agents such as propranolol [(1-(isopropylamino)-3-(1-naphthyloxy)-2 propranolol] inhibit response to adrenergic stimuli by competitively blocking beta-adrenergic receptors within the myocardium and within bronchial and vascular smooth muscle. Propranolol decreases heart rate and prevents exercise-induced increases in heart rate, decreases myocardial contractility, decreases cardiac output, increases systolic ejection time, and increases cardiac volume. The drug also decreases conduction velocity through the sinoatrial (SA) and atrioventricular (AV) nodes and decreases myocardial automaticity via beta-adrenergic blockade. These compounds are useful in the management of angina to reduce the frequency of anginal attacks, allow a decrease in nitrate dosage, and increase the patient's exercise tolerance.

Currently, propranolol is used for the management of various cardiac arrhythmias and as monotherapy or in combination with other classes of antihypertensive agents for management of hypertension. Other uses include migraine prophylaxis, essential tremor, secondary prevention of myocardial infarction, reduction in the risk of cardiovascular mortality in patients who have survived the acute phase of myocardial infarction, hypertrophic subaortic stenosis, pheochromocytoma, thyrotoxicosis, and anxiety. Propranolol has been used in the management of cyanotic spells of Fallot's tetralogy, bleeding in patients with cirrhosis, acute exacerbations of schizophrenia, and tremors associated with lithium therapy.

Propranolol is a biopharmaceutical class I agent that is freely soluble in water with a high permeability characterized by rapid and almost complete absorption following oral administration. A major drawback of oral propranolol is extensive metabolism so that only a small proportion reaches the systemic circulation. Peak plasma concentrations occur 60–90 minutes after oral administration of the conventional tablets, necessitating administration three or four times daily. A sustained release form of propranolol for once daily administration is available and is marketed by the Wyeth-Ayerst Company under the trade name INDERAL® LA.

Sustained release tablet or capsule forms of propranolol comprising coated propranolol HCL pellets are described in U.S. Pat. Nos. 5,968,554, 4,898,737, 4,248,856, 4,248,857, 4,248,848, 4,309,404, 4,309,405, 4,309,406, 4,728,512, 4,780,318 and spheroids made from propranolol in admixture with microcrystalline cellulose are described in U.S. Pat. No. 4,138,475. The present invention relates to a new sustained release pharmaceutical composition made of sugar spheres which is not disclosed in, nor rendered obvious by, said patents nor elsewhere in the art.

Numerous techniques are in the prior art for preparing sustained or controlled release pharmaceutical formulations. One common technique involves surrounding an osmotically active drug core with a semipermeable membrane. The drug is released from the core over time by allowing a fluid such as gastric or intestinal fluid to permeate the coating membrane and dissolve the drug so the dissolved drug can permeate the membrane. In some cases a hydrogel is employed to push the active ingredient through the passageway in the membrane.

Another common technique for preparing controlled release pharmaceutical formulations is to encapsulate a plurality of beads, pellets or tablets that are coated with varying levels of a diffusion barrier and/or different types of the diffusion barriers. Release of the pharmaceutical may occur by leaching, erosion, rupture, diffusion or similar actions depending on the nature and thickness of the coating material. These products require multi-layered coating, sometimes as much as 30 to 90 coats.

Film coating techniques are characterized by the deposition of a uniform film onto the surface of a substrate. Because of the capability of depositing a variety of coating materials onto solid cores, this process has been used to make controlled release dosage forms starting from different formulations, such as tablets, granules, pellets and capsules. Cores are usually prepared using one of the following processes: compaction, surface-layering, agglomeration or extrusion-spheronization.

The current surface-layering technique for pelletization involves the use of inert substrates and their enlargement by intermittently spraying a binder solution and applying the active substance powder in a rotating coating pan or in a fluidized bed. This current procedure still presents drawbacks. The powder layering process requires a great deal of repetition of wetting and powdering operations and is thus time consuming. Undesired agglomeration such as the formation of seedless drug agglomerates of various sizes and adhesion of the pellets to the wall of the coating equipment can occur producing a high loss of drug. Additionally, the powder layering technique requires specialized equipment such as a rotary-tangential fluidized bed or modified rotating pans. To this end, the present invention relates to a pelletization process, typified by the application of a beta-adrenergic-blocking agent/water insoluble binder solution to an inert core followed by application of a sustained release coating. It is an object of the present invention to provide a controlled or sustained release dosage formulation for beta-adrenergic blocking agents, preferably propranolol, or its pharmaceutically acceptable salt, that is easy to manufacture and can be used to prepare a range of dosing levels suitable for once daily administration.

It is a further object of the present invention to provide a controlled or sustained release dosage form for beta-adrenergic blocking agents, preferably propranolol, or its pharmaceutically acceptable salt, characterized by a high extent of absorption, which is largely invariable from individual to individual, and hence by a high bioavailability that can provide therapeutic levels of the drug to an animal or human in need of such treatment over a twelve to twenty-four hour period.

SUMMARY OF THE INVENTION

This invention relates to a novel oral drug delivery formulation and a method for preparing the drug delivery formulation.

The foregoing objectives are met by a controlled release capsule containing pellets comprising:
(a) a core comprising:
(i) a beta-adrenergic blocking agent;
(ii) an inert pellet as a starting material;
(iii) a binder comprising a water insoluble or soluble polymer; and
(iv) optionally, a filler; and
(b) a coating comprising:
(i) a water soluble first polymer;
(ii) a water insoluble second polymer;
(iii) a plasticizer; and
(iv) an antisticking agent.

The core comprises about 85 to 99.5 weight percent of the total dosage form and preferably about 90 to 98.5 weight percent of the dosage form.

The beta-adrenergic blocking agent comprises about 30 to about 75 weight percent of the total dosage form, preferably 40 to 65 and most preferably about 45 to 60 weight percent of the dosage form.

The dosage form of the present invention can provide therapeutic levels of propranolol for twelve to twenty-four hour time periods and does not obtain peak plasma levels for at least 4 hours, ideally 5–8 hours after administration.

DESCRIPTION OF THE PREFERRED EMBODIMENTS

The term beta-adrenergic blocking agent as used in this specification refers to acebutolol, atenolol, bisoprolol, metoprolol, nadolol, sotalol, timolol, betaxolol, labetalol, penbutolol, pindolol, carteolol, esmolol or their pharmaceutically acceptable derivatives, salts and stereoisomers. Other examples are described in Ame.10rican Society of Health-System Pharmacists, Drug Information 2001 and are incorporated herein by reference. The preferred beta-adrenergic blocking agent is propranolol as described in U.S. Pat. No. 3,337,628 or a pharmaceutically acceptable derivative, salt or stereoisomer thereof.

The inert pellet starting material can be any type of commonly known pellet starting material such as a starch or sugar sphere having a diameter ranging from about 15–50 mesh, preferably about 30–40 mesh. The preferred pellet starting material is sugar spheres, NF containing not less than 62.5 percent and not more than 91.5 percent of sucrose. The spheres should have consistent bulk density, low friability, and low dust generation properties.

The binder must possess high adhesivity and an appropriate viscosity, to guarantee good adhesion between the sugar cores and propranolol particles, resulting in a high concentration of drug in the pellets. The binding agents employed can be any type of water insoluble or soluble binding agent commonly known in the art such as hydroxypropyl methylcellulose (HPMC), povidone, hydroxypropyl cellulose (HPC), polymethacrylates or ethylcellulose. In the preferred embodiment of the present invention, the binding agent is a water insoluble polymer such as ethylcellulose having a viscosity in the range of 8–12 cps at 20 degrees C., preferably 9–11 cps and most preferably about 10 cps.

A suitable filler should have a particle size of about 20 µm (microns). Non-swellable microcrystalline cellulose, such as the material sold as Avicel PH-105 or Vivapur Type 99 is the filler used in the preferred embodiment. The ratio of filler to binder can range from about 0.5:5.0 to about 2.0:0.5. The preferred ratio is about 4.33:1 (wt/wt) of microcrystalline cellulose and ethylcellulose in the drug loaded active pellets.

The core of the present invention will comprise the following ingredients:

| INGREDIENT | PREFERRED | MOST PREFERRED |
|---|---|---|
| Beta-adrenergic blocking agent | 30–70% | 45–55% |
| Filler | 20–50% | 25–35% |
| Binder | 1–15% | 3–10% |
| Inert pellet | 5–25% | 7.5–15% |

All the percentages in the above table are based on the total weight of the core.

The core of the present invention which comprises the beta-adrenergic blocking agent is prepared by forming a suspension of the binder, drug and other ingredients, and then layering the suspension onto the starting inert pellets using any of the layering techniques known in the industry such as fluidized bed coating, rotor granulation or pan coating.

The controlled release coating layer that is applied to the core to control the release of the drug from the dosage form comprises a water insoluble polymer, a water soluble polymer, a plasticizer, and an antisticking agent. Preferably, the amount of water insoluble polymer in the coating is greater than the amount of water soluble polymer in the coating.

The controlled release coating may be manufactured from a variety of water insoluble polymers typically utilized in the pharmaceutical arts such as, for example, ethylcellulose, cellulose acetate, cellulose propionate, cellulose acetate butyrate, polyethylene, polypropylene, polyethylene oxide, polyvinyl acetate, polyvinyl chloride, acrylate polymers and their derivatives, such as Eudragit.

A suitable form of ethylcellulose for the controlled release coating is that having a viscosity ranging from 7 cps to 50 cps at 20° C. When ethylcellulose is employed in both the core and the coating, the viscosity of the ethylcellulose in the coating can be the same as or different from the ethylcellulose in the core.

A small portion of a water soluble polymer is included in the controlled release coating. Examples of such polymers include methylcellulose, hydroxypropyl cellulose, hydroxypropyl methylcellulose, polyethylene glycol, polyvinyl pyrrolidone. Hydroxypropyl methylcellulose is the preferred polymer in this invention.

In order to promote a high separation of the pellets during processing, an antisticking agent was added to the controlled release coating. Suitable antisticking agents that can be used in the present invention are talc, magnesium stearate, silicon dioxide, glycerol monostearate, kaolin or a mixture of the forgoing. The antisticking agent prevents the pellets from sticking to one another during processing. The antisticking agent may be dusted onto the active pellets during the coating process or it may be incorporated into the controlled release coating suspension and applied with the controlled release coating suspension.

A plasticizer is used to impart flexibility to the controlled release coating. The effectiveness of a plasticizer for a particular polymer dispersion depends on the plasticizer/polymer compatibility and the permanence of the plasticizer in the film during coating, storage, and during contact with biological fluids. Examples of suitable plasticizers include acetyl triethyl citrate, dibutyl phthalate, tributyl citrate, triethyl citrate, acetyl tributyl citrate, propylene glycol, triacetin, polyethylene glycol and diethyl phthalate. In this invention, the preferred plasticizer is acetyl tributyl citrate.

The controlled release coating layer can be applied by any means commonly known in the industry, however, if the antisticking agent is to be dusted onto the cores during the coating process, it is preferred to use a rotary granulator or pan coater for the coating process. If the antisticking agent is applied by suspending it in the coating solution, it is preferred to use a fluidized bed coater or rotary granulator for the coating process.

The quantity of coating to be applied to give the desired release characteristics of the cores can vary widely and will depend on the particular polymer or mixture thereof chosen. This amount can be readily determined by one skilled in the art using dissolution profile data.

In a preferred embodiment the coating of the present invention will have the following composition:

| COATING: | Preferred | Most Preferred |
| --- | --- | --- |
| water insoluble polymer | 40–90% | 55–75% |
| plasticizer | 0–15% | 5–10% |
| water soluble polymer | 1–25% | 5–20% |
| antisticking agent | 0–20% | 5–15% |

The forgoing percentages are based on the total weight of the coating.

The controlled release dosage forms prepared in accordance with the present invention should exhibit the following dissolution profile when tested in a USP type II apparatus at 75 rpm in simulated gastric fluid and at 37° C.:

| Time (hours) | Preferred | Most Preferred |
| --- | --- | --- |
| 2 | 10–40% | 15–35% |
| 4 | 35–65% | 40–60% |
| 8 | 65–85% | NLT 70% |
| 12 | NLT 70% | NLT 75% |
| 16 | NLT 80% | NLT 85% |
| 20 | NLT 85% | NLT 90% |

NLT = NOT LESS THAN

The controlled release dosage form prepared according to the present invention should further exhibit the following dissolution profile when tested in a USP type II apparatus at 75 rpm in 900 ml of simulated intestinal fluid (pH 6.8 phosphate buffer) and at 37° C.:

| Time (hours) | Preferred | Most Preferred |
| --- | --- | --- |
| 2 | 10–40% | 15–30% |
| 4 | 35–65% | 45–60% |
| 8 | 45–85% | 55–80% |
| 12 | NLT 70% | NLT 75% |
| 16 | NLT 80% | NLT 85% |
| 20 | NLT 85% | NLT 90% |

During all the preparation steps, no sign of drug degradation was detectable. A one month accelerated conditions stability study was performed to study the effect of storage on the formulation. The dissolution of the propranolol formulation was unaffected by storage under accelerated conditions over a one month period.

The following example illustrates the present invention and is not intended to limit the scope of the present invention.

EXAMPLE 1

A 3 kg batch of the formulation was manufactured using all materials which comply with current USP/NF compendial specifications.

A controlled release oral propranolol dosage form in accordance with the present invention is prepared by form ing an active or immediate release core having the following composition:

| I ACTIVE CORE | |
| --- | --- |
| propranolol HCL, USP[1] | 52.92% |
| sugar sphere, NF[2] | 19.37% |
| microcrystalline cellulose, NF | 22.5% |
| ethylcellulose (ETHOCEL 10 cps) | 5.21% |

[1]racemic mixture with an average particle size of less than 75 microns.
[2]30/35 mesh.

The active core is prepared by adding 0.156 kg of the ethylcellulose into a solution containing 2.752 kg of isopropyl alcohol, USP and ethanol SDA 3A-190 Proof while mixing with a homogenizer. Once the ethylcellulose is dissolved, 1.2 kg of propranolol is added to the above solution while mixing for 20 minutes until a uniform suspension is obtained. While homogenizing, 0.675 kg of microcrystalline cellulose is added to the suspension. After homogenizing the suspension for 10 minutes, the homogenizer is replaced with a mechanical stirrer. The ethylcellulose/microcrystalline cellulose/propranolol suspension is then applied to 0.969 kg of the sugar spheres in a fluidized bed coater under the following conditions: product temperature between 20–30° C.; atomization pressure is 1.5–2.5 bars; and the pump rate is 10–80 ml/min.

After all the ethylcellulose/microcrystalline cellulose/propranolol suspension is consumed, the in-process propranolol active pellets will contain approximately 40% propranolol based upon the total weight of the in-process active pellet. The in-process propranolol active pellets are then coated with a second batch of ethylcellulose/microcrystalline cellulose/propranolol suspension that is prepared as described above and coated onto the in-process propranolol active pellets in a fluidized bed coater as described above until the propranolol active pellets comprise approximately 53% propranolol based upon the total weight of the final propranolol active pellet.

Once the target amount of propranolol is applied to the active cores, the active cores are dried in the fluidized bed coater for approximately 15+/−10 minutes or until the LOD (loss on drying) is less than 1%. Once the drying stage is completed, the dried propranolol active pellets are placed in a clean, properly labeled double polyethylene bag lined container.

The active cores are coated with a controlled release coating wherein the controlled release coating has the following composition:

| II SUSTAINED RELEASE COATING | |
| --- | --- |
| ethylcellulose, NF (ETHOCEL standard 45 premium) | 75.00% |
| acetyl tributyl citrate | 7.5% |
| hydroxypropyl methylcellulose, USP (METHOCEL E5) | 7.5% |
| talc, USP | 10.00% |

The controlled release coating is prepared by adding 9.15 g of the ethylcellulose to a solution of 46.81 g of isopropyl alcohol and 43.61 g of acetone while mixing with a stirrer until it is completely dissolved. Add 0.92 g of acetyltributyl citrate while stirring continuously for 2 minutes. Add 0.92 g of hydroxypropyl methylcellulose (HPMC) to the solution while stirring until it is completely dissolved. Add 1.22 g of talc to the solution while stirring for 10 minutes or until completely dispersed. The controlled release coating suspension is then applied to the active cores using a Glatt rotary granulator under the following conditions: rotor speed of 175+/−5 rpm; inlet temperature of 25–30° C.; atomization of 1–2 bar; and a pump rate of 3–20 ml/min. The coating is continued until a theoretical coating of approximately 3.3% is obtained.

After the theoretical coating level is obtained the coated cores are dried in the fluidized bed coater for 15 minutes and then milled through 12 and 25 mesh screens. Over and under-sized pellets were discarded. The recovery of pellets was 98%. The pellets are then encapsulated into hard gelatin capsules size number 00, resulting in a final 160 mg of propranolol per capsule.

The controlled release coated pellets have the following composition:

| III CONTROLLED RELEASE COATED PELLETS | |
| --- | --- |
| sugar sphere | 18.73% |
| propranolol HCL | 51.17% |
| microcrystalline cellulose (AVICEL PH 105) | 21.76% |
| ethylcellulose (ETHOCEL 10 cps) | 5.04% |
| ethylcellulose (standard 45 premium) | 2.48% |
| acetyl tributyl citrate | 0.25% |
| HPMC (METHOCEL E5) | 0.25% |
| talc | 0.33% |

The drug release rate from the controlled release pellets were determined according to the procedures reported in USP XXIII (Apparatus II, 75 rpm, 37° C., and pH 6.8). The pellets were found to have the following release profile:

| Time (hours) | % Released |
| --- | --- |
| 2 | 36 |
| 4 | 55 |
| 6 | 63 |
| 8 | 70 |
| 12 | 78 |
| 16 | 81 |

The resulting controlled release coated pellets were encapsulated into hard gelatin capsules and were tested in a simulated gastric fluid according to the procedure described in United States Pharmacopoeia XXIII, using Apparatus II @ 75 rpm and found to have the following release profile:

| Time (hours) | % Released |
| --- | --- |
| 2 | 21 |
| 4 | 43 |
| 6 | 58 |
| 8 | 73 |
| 12 | 85 |
| 16 | 93 |
| 20 | 97 |

Figure 1:
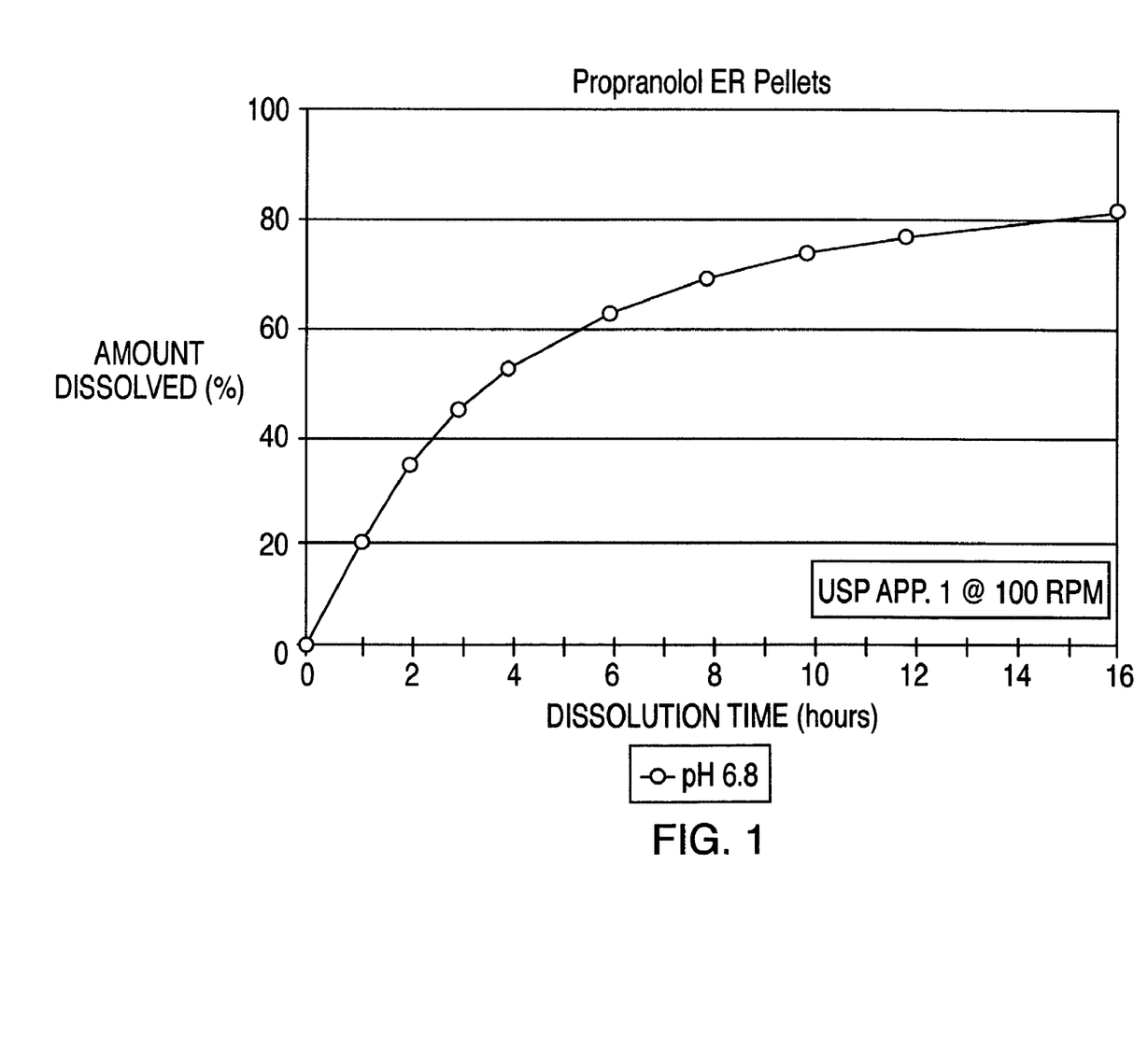
FIG. 1 is a graph depicting the dissolution profile in simulated intestinal fluid (pH 6.8) of the formulation described in Example 1 when tested according to the procedure described in United States Pharmacopoeia XXIII, Apparatus 1 @ 100 rpm.
Figure 2:
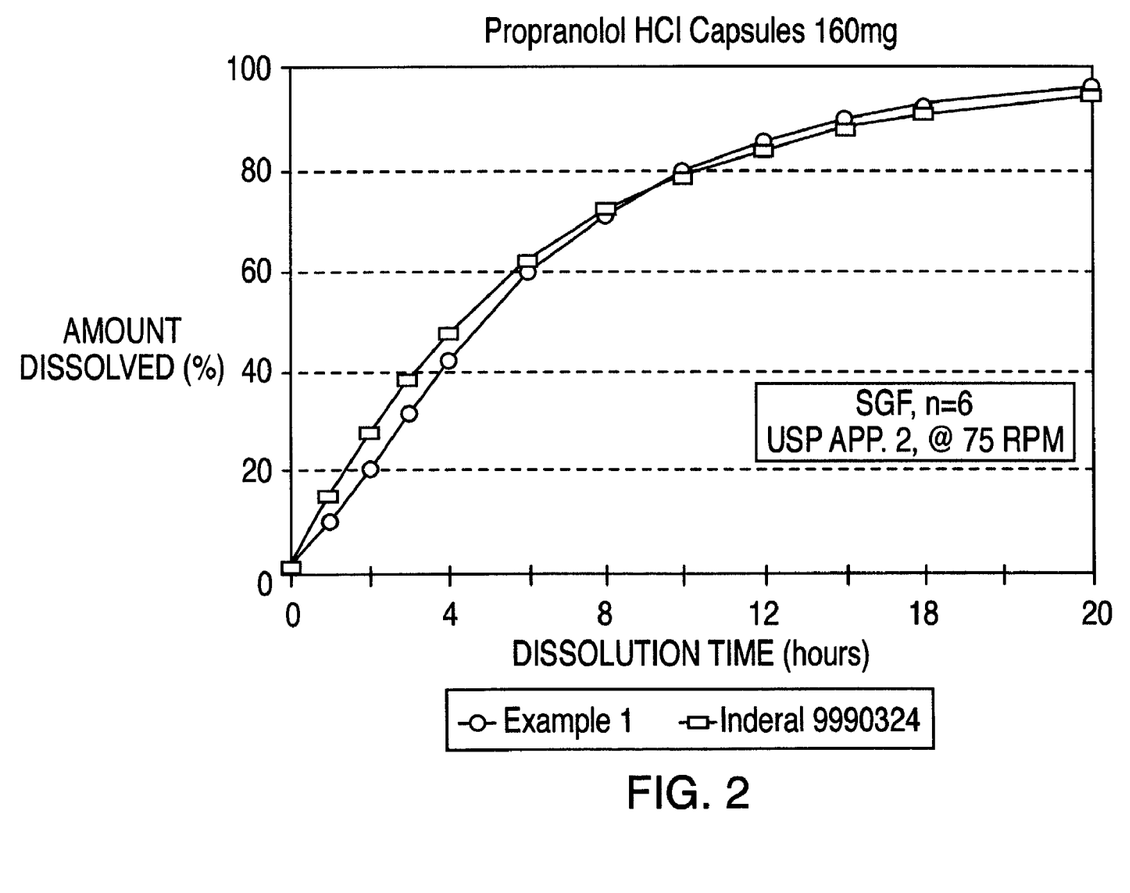
FIG. 2 is a graph depicting the dissolution profile in simulated gastric fluid of the formulation capsules described in Example 1 and a commercially available formulation of propranolol, INDERAL® LA when tested according to the procedure described in United States Pharmacopoeia XXIII, Apparatus 1 @ 100 rpm.

The release profiles of the controlled release product prepared in this Example are shown in FIGS. 1 and 2.

The bioavailability of the controlled release propranolol formulation prepared in this Example has been determined under both fed and fasting conditions. Two panels of eight subjects each were randomly assigned to receive either the propranolol formulation described herein or INDERAL®

LA in an open, randomized single dose study. Blood samples were collected over a 48-hour period and analyzed for propranolol concentrations with a validated HPLC method using florescence detection and solid phase extraction. The blood level studies carried out and the results of which are given in Tables 1 and 2 show that the dissolution of a 160 mg single dose of the controlled release propranolol formulation prepared in Example 1 and INDERAL® LA is similar under both fed and fasting conditions. Under fasting conditions, the mean Cmax and AUC for the Example 1 formulation were 37.69 µg/L and 565.7 µg/L, and for the INDERAL® LA were found to be 46.8 µg/L and 745.9 µg/L. Under fed conditions, the mean Cmax and AUC for the Example 1 formulation were 79.5 µg/L and 1231.5 µg/L, and for the INDERAL® LA were found to be 77.9 µg/L and 1300.9 µg/L.

Figure 3:
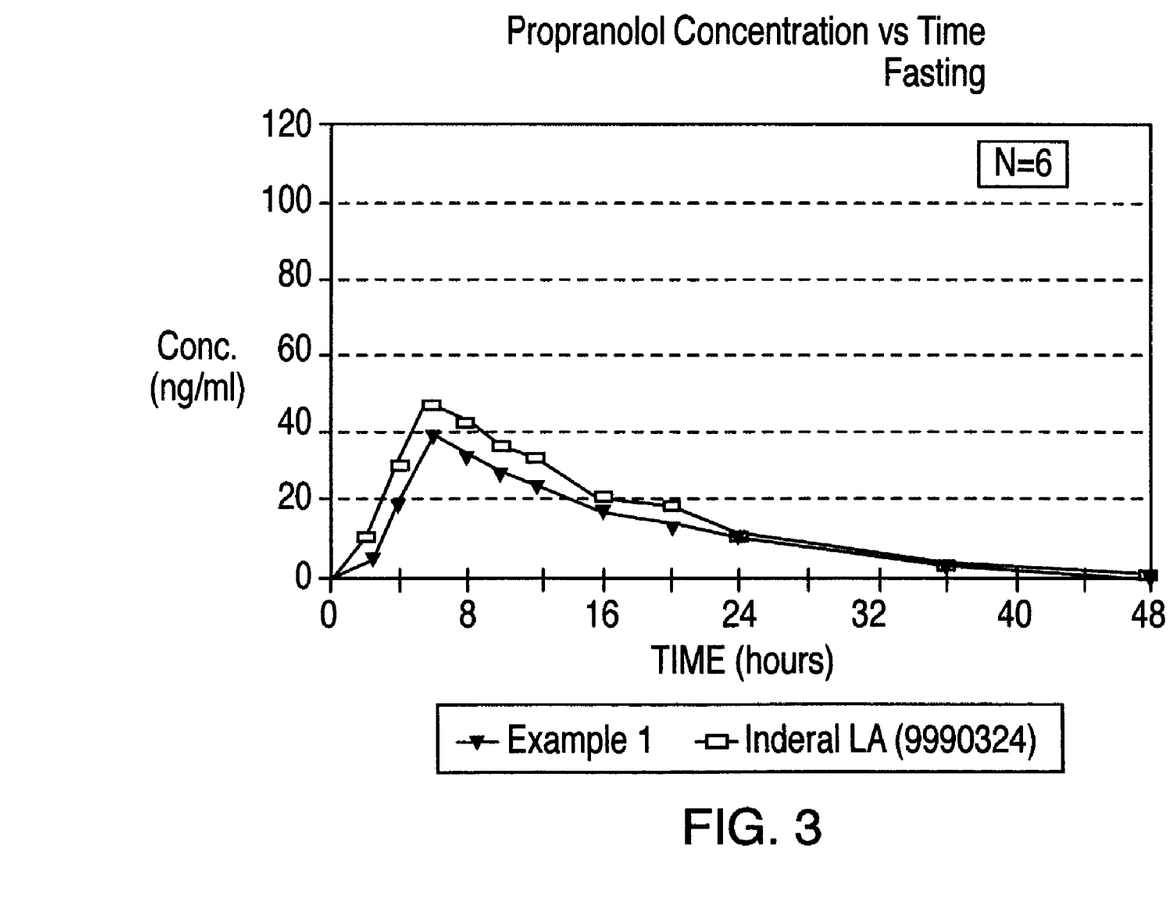
FIG. 3 is a graph depicting the linear plot of the mean plasma propranolol concentration vs. time of the formulation described in Example 1 and the linear plot of the mean plasma propranolol concentration versus time of the commercially available formulation of propranolol, IDERAL LA® under fasting conditions.

FIG. 3 depicts the in vivo propranolol plasma profile of the controlled release product prepared in Example 1. Also shown in FIG. 3 is the in vivo propranolol plasma profile of INDERAL® LA.

Table 1 is a summary of the bioavailability comparison data under fasting conditions, test/reference ratio, shown in FIG. 3 wherein the INDERAL® LA product is the reference product in a two way crossover biostudy with n=8.

TABLE 1

|  | Test Mean | Ref Mean | G-Mean Ratio |
|---|---|---|---|
| Cmax | 37.69 | 46.78 | 0.803 |
| $AUC^{inf}$ | 565.70 | 745.90 | 0.784 |

Figure 4:
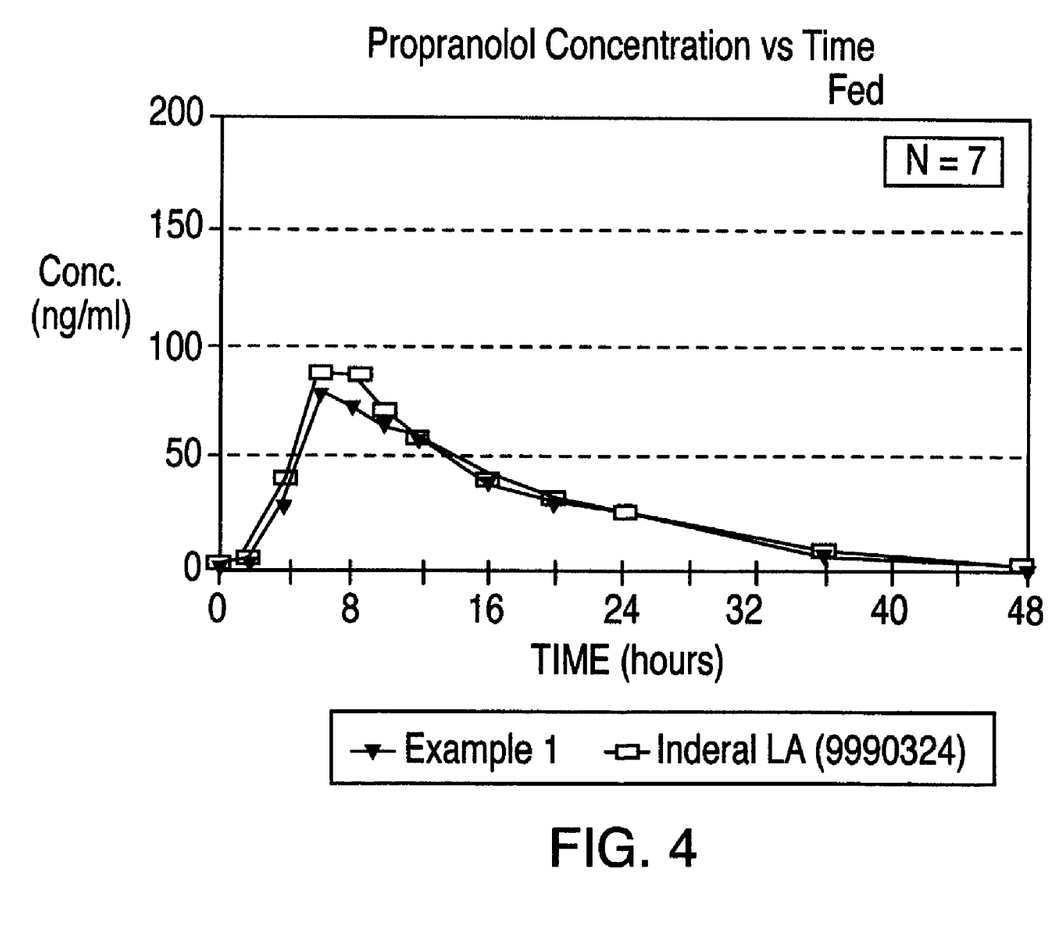
FIG. 4 is a graph depicting the linear plot of the mean plasma propranolol concentration vs. time of the formulation described in Example 1 and the linear plot of the mean plasma propranolol concentration versus time of the commercially available form of propranolol, INDERAL LA® under fed conditions.

Table 2 is a summary of the bioavailability comparison data under non-fasting conditions, test/reference ratio, shown in FIG. 4 wherein the INDERAL® LA is the reference product in a two way crossover biostudy with n=7.

TABLE 2

|  | Test Mean | Ref Mean | G-Mean Ratio |
|---|---|---|---|
| Cmax | 79.50 | 95.64 | 0.901 |
| $AUC^{inf}$ | 1231.50 | 1300.97 | 0.979 |

EXAMPLE 2

A 20.4 kg batch of the formulation was manufactured using all materials which comply with current USP/NF compendial specifications.

A controlled release oral propranolol dosage form in accordance with the present invention is prepared by forming an active or immediate release core having the following composition:

| I ACTIVE CORE | |
|---|---|
| propranolol HCL, USP[1] | 52.92% |
| sugar sphere, NF[2] | 10.43% |
| microcrystalline cellulose, NF | 29.77% |
| ethylcellulose (ETHOCEL 10 cps) | 6.88% |

[1] racemic mixture with an average particle size of less than 75 microns.
[2] 35/40 mesh.

The active core is prepared by adding 1.33 kg of the ethylcellulose into a solution containing isopropyl alcohol, USP and ethanol SDA 3A-190 Proof while mixing with a homogenizer. Once the ethylcellulose is dissolved, 10.11 kg of propranolol is added to the above solution while mixing for 20 minutes until a uniform suspension is obtained. While homogenizing, 5.68 kg of microcrystalline cellulose is added to the suspension. After homogenizing the suspension for 10 minutes, the homogenizer is replaced with a mechanical stirrer. The ethylcellulose/microcrystalline cellulose/propranolol suspension is then applied to 1.99 kg of the sugar spheres in a fluidized bed coater under the following conditions: product temperature between 20–30° C.; atomization pressure is 1.5–2.5 bars; and the pump rate is 10–80 ml/min.

After all the ethylcellulose/microcrystalline cellulose/propranolol suspension is consumed, the in-process propranolol active pellets will contain approximately 40% propranolol based upon the total weight of the in-process active pellet. The in-process propranolol active pellets are then coated with a second batch of ethylcellulose/microcrystalline cellulose/propranolol suspension that is prepared as described above and coated onto the in-process propranolol active pellets in a fluidized bed coater as described above until the propranolol active pellets comprise approximately 53% propranolol based upon the total weight of the final propranolol active pellet.

Once the target amount of propranolol is applied to the active cores, the active cores are dried in the fluidized bed coater for approximately 15+/–10 minutes or until the LOD (loss on drying) is less than 1%. Once the drying stage is completed, the dried propranolol active pellets are placed in a clean, properly labeled double polyethylene bag lined container.

The active cores are coated with a controlled release coating wherein the controlled release coating has the following composition:

| II SUSTAINED RELEASE COATING | |
|---|---|
| ethylcellulose, NF (ETHOCEL 10 cps) | 64.53% |
| acetyl tributyl citrate | 6.44% |
| hydroxypropyl methylcellulose, USP (METHOCEL E5) | 16.13% |
| talc, USP | 12.91% |

The controlled release coating is prepared by adding 0.839 kg of the ethylcellulose to a solution of 3.45 kg of isopropyl alcohol and 6.90 kg of acetone while mixing with a stirrer until it is completely dissolved. Add 0.084 kg of acetyltributyl citrate while stirring continuously for 2 minutes. Add 0.209 kg of hydroxypropyl methylcellulose (HPMC) to the solution while stirring until it is completely dissolved. Add 0.168 kg of talc to the solution while stirring for 10 minutes or until completely dispersed. The controlled release coating suspension is then applied to the active cores using a Glatt rotary granulator under the following conditions: rotor speed of 175+/–5 rpm; inlet temperature of 25–30° C.; atomization pressure of 1–2 bar; and a pump rate of 3–20 ml/min. The coating is continued until a theoretical coating of approximately 3.3% is obtained.

After the theoretical coating level is obtained the coated cores are dried in the fluidized bed coater for 15 minutes and then milled through 12 and 25 mesh screens. Over and under-sized pellets were discarded. The recovery of pellets was 98%. The pellets are then encapsulated into hard gelatin capsules size number 00, resulting in a final 160 mg of propranolol per capsule.

The controlled release coated pellets have the following composition:

| III CONTROLLED RELEASE COATED PELLETS | |
|---|---|
| sugar sphere | 9.75% |
| propranolol HCL | 49.56% |
| microcrystalline cellulose (Vivapur Type 99) | 27.84% |
| ethylcellulose (ETHOCEL 10 cps) | 6.42% |
| ethylcellulose (ETHOCEL 10 cps) | 4.11% |
| acetyl tributyl citrate | 0.419% |
| HPMC (METHOCEL E5) | 1.028% |
| talc | 0.824% |

The drug release rate from the controlled release pellets were determined according to the procedures reported in USP XXIII (Apparatus I, 100 rpm, 37° C., and pH 6.8). The pellets were found to have the following release profile:

| Time (hours) | % Released |
|---|---|
| 2 | 34 |
| 4 | 55 |
| 6 | 67 |
| 8 | 76 |
| 12 | 83 |
| 16 | 92 |

The resulting controlled release coated pellets were encapsulated into hard gelatin capsules and were tested in a simulated gastric fluid according to the procedure described in United States Pharmacopoeia XXIII, using Apparatus I @ 100 rpm and found to have the following release profile:

| Time (hours) | % Released |
|---|---|
| 2 | 30 |
| 4 | 52 |
| 6 | 68 |
| 8 | 78 |
| 12 | 89 |
| 16 | 97 |

Figure 5:
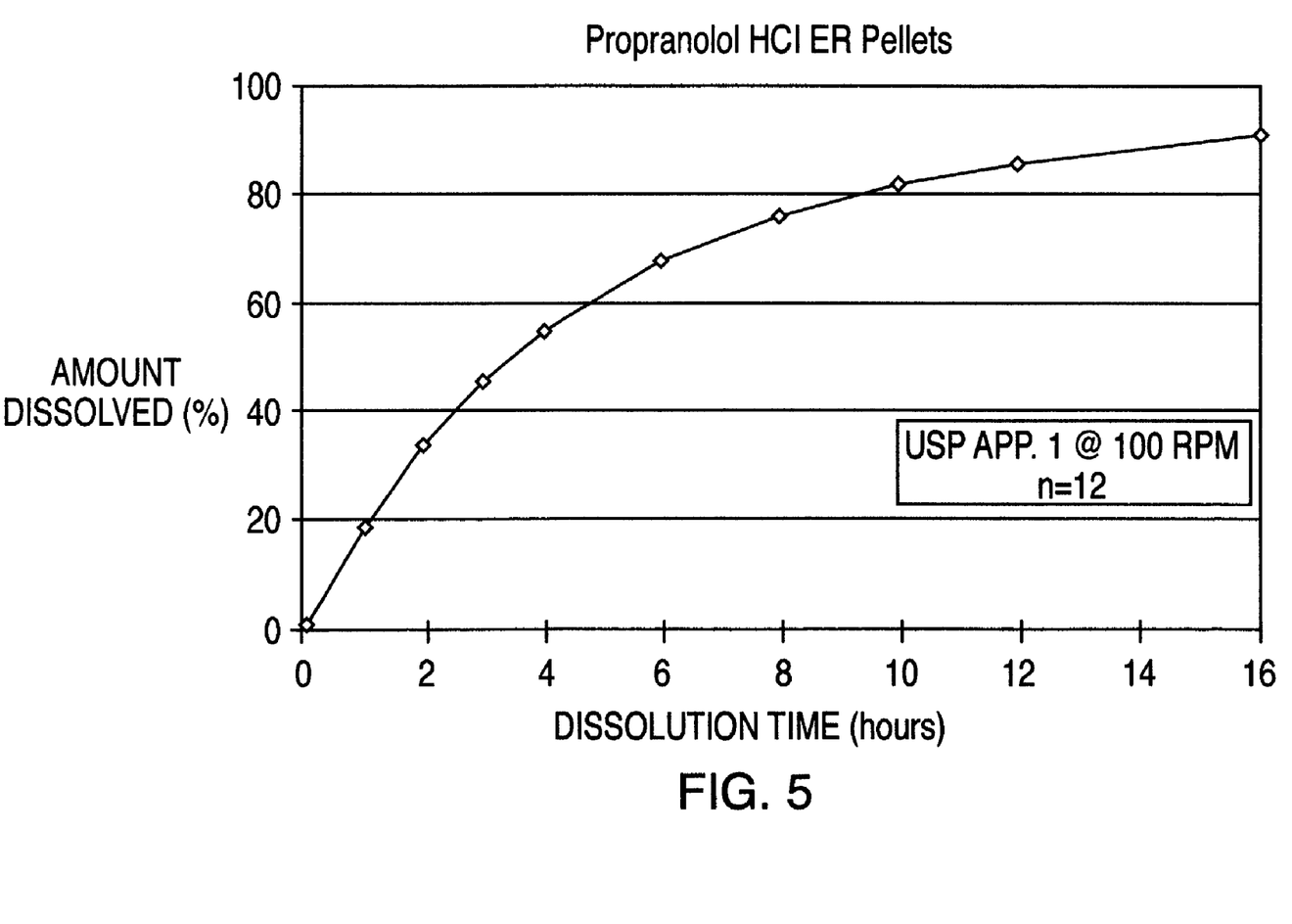
FIG. 5 is a graph depicting the dissolution profile in simulated intestinal fluid of the formulation pellets described in Example 2 and tested according to the procedure described in United States Pharmacopoeia XXIII, Apparatus 1 @ 100 rpm.
Figure 6:
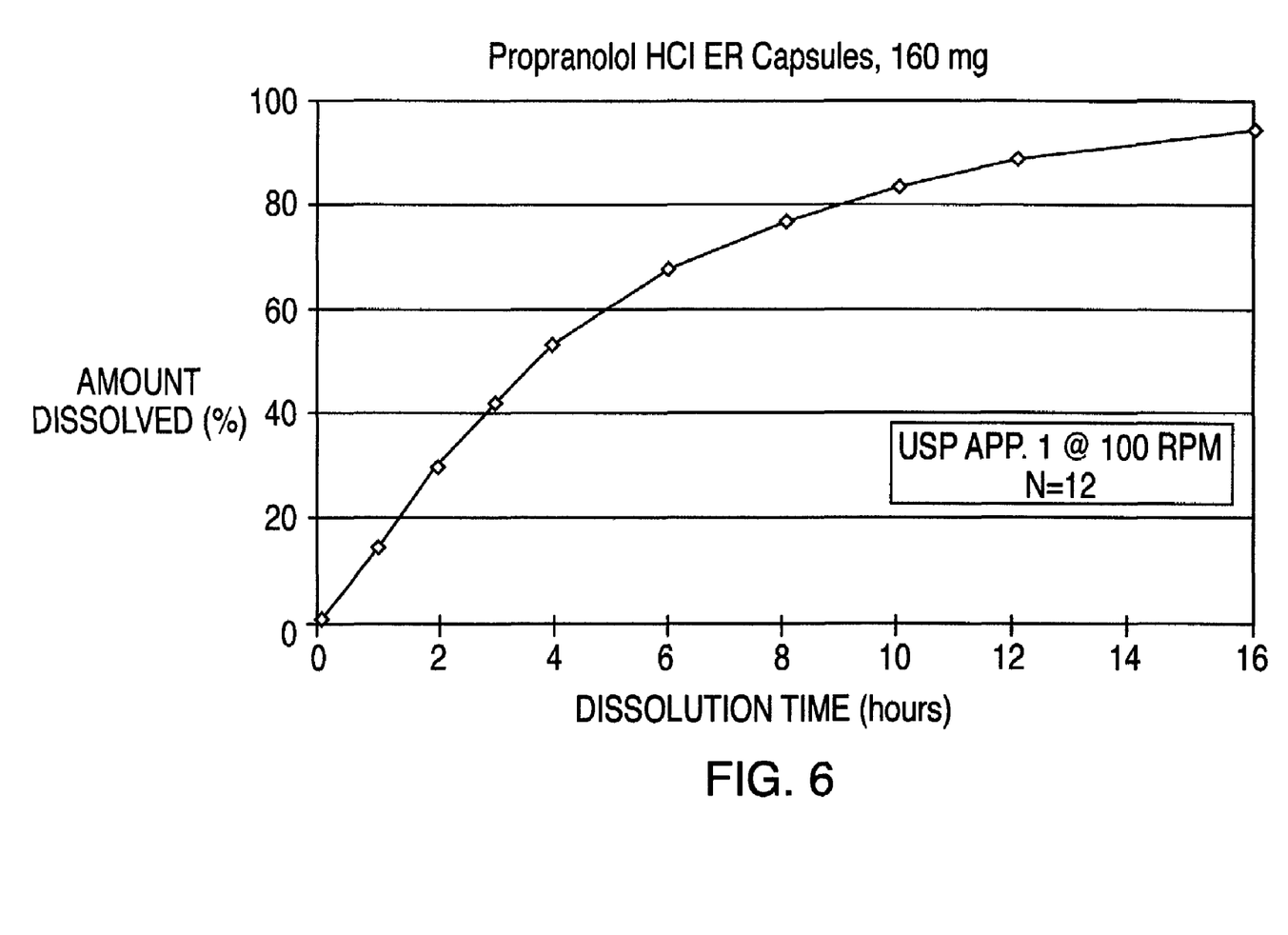
FIG. 6 is a graph depicting the dissolution profile in simulated intestinal fluid of the propranolol extended release capsules described in Example 2 and tested according to the procedure described in United States Pharmacopoeia XXIII, Apparatus 1 @ 100 rpm.

The release profiles of the controlled release product prepared in this Example are shown in FIGS. 5 and 6.

The bioavailability of the controlled release propranolol formulation prepared in this Example has been determined under both fed and fasting conditions. Two panels of eight subjects each were randomly assigned to receive either the propranolol formulation described herein or INDERAL® LA in an open, randomized single dose study. Blood samples were collected over a 48-hour period and analyzed for propranolol concentrations with a validated HPLC method using florescence detection and solid phase extraction. The blood level studies carried out and the results of which are given in Tables 3 and 4 show that the dissolution of a 160 mg single dose of the controlled release propranolol formulation prepared in Example 2 and INDERAL® LA is similar under both fed and fasting conditions. Under fasting conditions, the G-mean for the Cmax was 0.979 and the G-mean for the AUC for the Example 2 formulation were 0.911. Under fed conditions, the G-mean for the Cmax was 1.28 and the G-mean for the AUC was 1.10.

Figure 7:
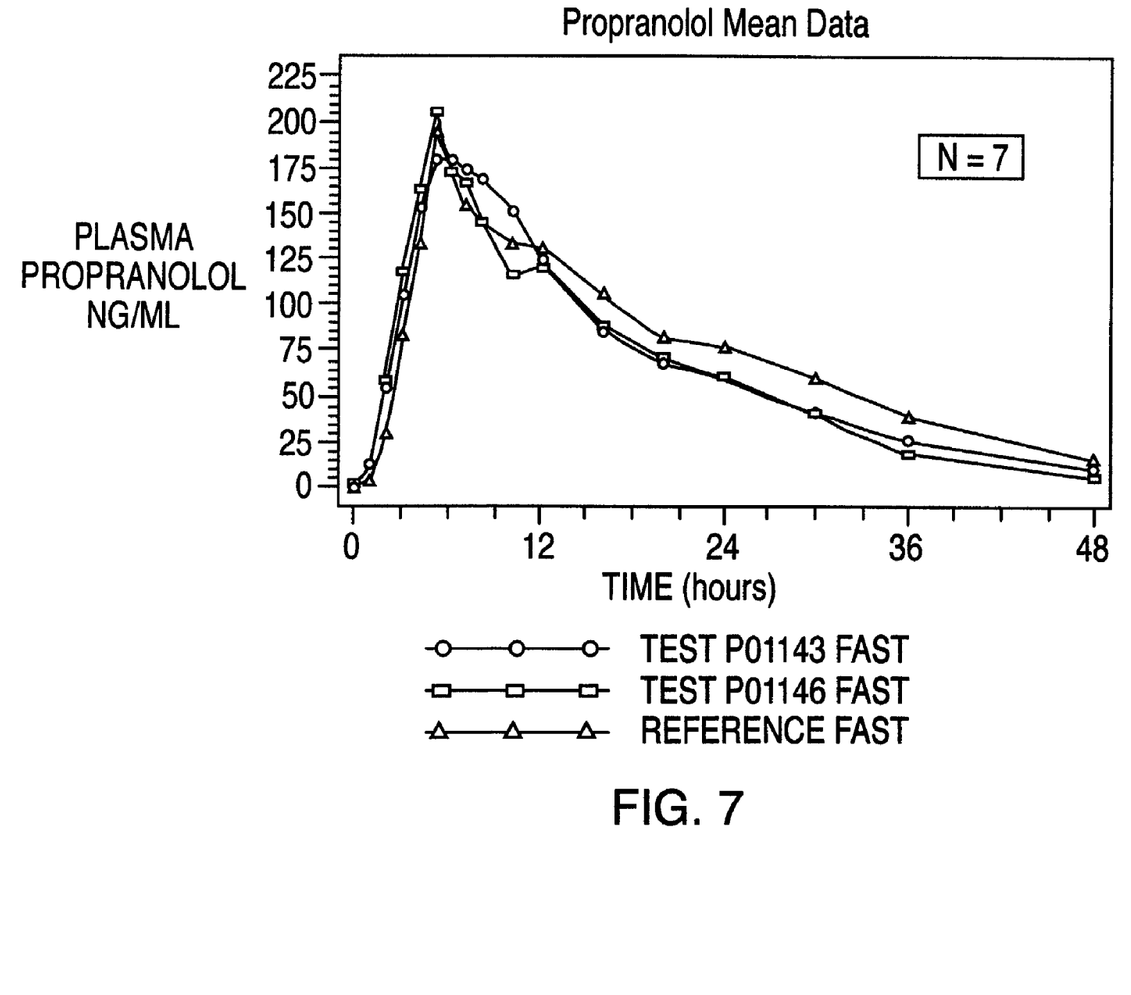
FIG. 7 is a graph depicting the linear plot of the mean propranolol concentration vs. time of the formulation described in Example 2 and the linear plot of the mean plasma propranolol concentration versus time of the commercially available formulation of propranolol, INDERAL LA® under fasting conditions.
Figure 8:
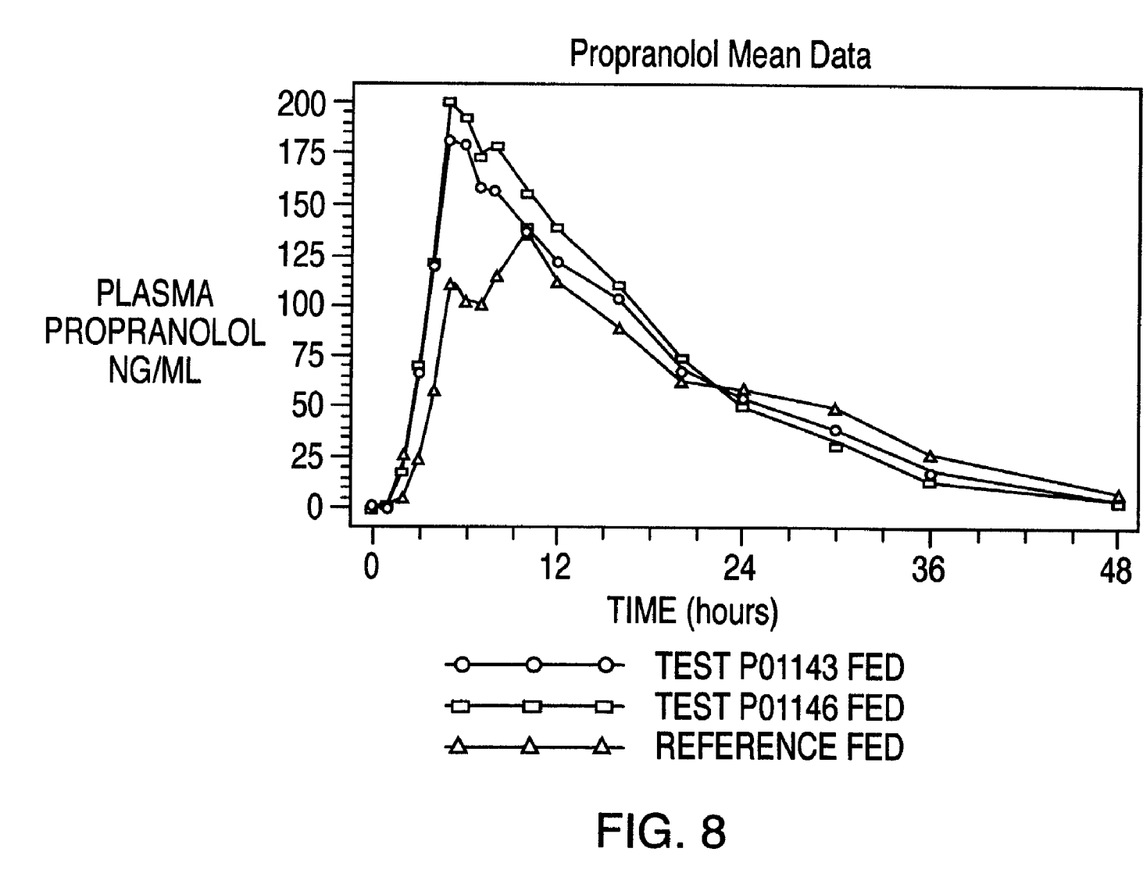
FIG. 8 is a graph depicting the linear plot of the mean propranolol concentration vs. time of the formulation described in Example 2 and the linear plot of the mean plasma propranolol concentration versus time of the commercially available formulation of propranolol, INDERAL LA® under fed conditions.

Table 2 is a summary of the bioavailability comparison data under fasting and fed conditions, test/reference ratio, shown in FIGS. 7 and 8, respectively, wherein the INDERAL® LA product is the reference product in a two way crossover biostudy with n=8.

TABLE 2

| | G-Mean Ratio | |
|---|---|---|
| | Fasting | Fed |
| Cmax | 0.979 | 1.28 |
| $AUC^{inf}$ | 0.911 | 1.10 |

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A controlled release pharmaceutical dosage form comprising a plurality of pellets wherein the pellets consists essentially of:
   (a) a core consisting essentially of:
      (i) propranolol or a pharmaceutically acceptable derivative thereof;
      (ii) sugar spheres;
      (iii) microcrystalline cellulose; and
      (iv) ethylcellulose; and
   (b) a coating applied directly to the core consisting essentially of a mixture of:
      (i) ethylcellulose;
      (ii) hydroxypropyl methylcellulose;
      (iii) acetyl tributyl citrate; and
      (iv) talc, wherein the viscosity of the core ethylcellulose is 8–12 cps and the viscosity of the coating ethylcellulose is above 8 cps wherein the dosage form exhibits the following dissolution profile when tested in a USP type 1 apparatus at 100 rpm in 900 ml of simulated intestinal fluid (pH 6.8 phosphate buffer) at 37° C.:
   after 2 hours 15–40% of the propranolol or a pharmaceutically acceptable derivative thereof is released;
   after 4 hours 35–65% of the propranolol or a pharmaceutically acceptable derivative thereof is released;
   after 8 hours 40–80% of the propranolol or a pharmaceutically acceptable derivative thereof is released;
   not less than 70% of the propranolol or a pharmaceutically acceptable derivative thereof is released after 12 hours; and
   not less than 80% of the propranolol or a pharmaceutically acceptable derivative thereof is released after 16 hours.

2. The controlled release pharmaceutical dosage form as defined in claim 1 wherein the core consists essentially of:
   30–70% propranolol or a pharmaceutically acceptable derivative thereof;
   10–40% microcrystalline cellulose;
   1–15% ethylcellulose;
   10–35% sugar sphere, wherein the foregoing percentages are based on the total weight of the core; and the coating consists essentially of:
   50–90% ethylcellulose;
   acetyl tributyl citrate;
   1–20% hydroxypropyl methylcellulose; and talc, wherein the foregoing percentages are based on the total weight of the coating.

3. The controlled release pharmaceutical dosage form as defined in claim 2 wherein the core consists essentially of:
50–60% propranolol or a pharmaceutically acceptable derivative thereof;
20–30% microcrystalline cellulose;
3–10% ethylcellulose; and 15–30% inert pellet starting material; and the coating consists essentially of:
60–80% ethylcellulose;
5–10% acetyl tributyl citrate;
5–15% hydroxypropyl methylcellulose; and
5–15% of talc.

4. The controlled release pharmaceutical dosage form as defined in claim 1 that exhibits the following dissolution profile when tested in a USP type II apparatus at 75 rpm in 900 ml of simulated intestinal fluid (pH 6.8 phosphate buffer) and at 37° C.:
after 2 hours 15–30% of the propranolol or a pharmaceutically acceptable derivative thereof is released;
after 4 hours 45–60% of the propranolol or a pharmaceutically acceptable derivative thereof is released;
after 8 hours 55–85% of the propranolol or a pharmaceutically acceptable derivative thereof is released;
not less than 75% of the propranolol or a pharmaceutically acceptable derivative thereof is released after 12 hours; and
not less than 85% of the propranolol or a pharmaceutically acceptable derivative thereof is released after 16 hours.

5. A controlled release pharmaceutical dosage form comprising a plurality of pellets wherein the pellets consists essentially of:
(a) a core consisting essentially of:
(i) propranolol or a pharmaceutically acceptable derivative thereof;
(ii) sugar spheres;
(iii) miuocrystalline cellulose; and
(iv) ethylcellulose; and
(b) a coating applied directly to the core consisting essentially of a mixture of:
(i) ethylcellulose;
(ii) hydroxypropyl methylcellulose;
(iii) acetyl tributyl citrate; and talc, wherein the viscosity of the core ethylcellulose is 8–12 cps and the viscosity of the coating ethylcellulose is above 8 cps wherein the dosage form exhibits the following dissolution profile when tested in a USP type II apparatus at 75 rpm in 900 ml of simulated gastric fluid and at 37° C.:
after 2 hours 10–40% of the propranolol or a pharmaceutically acceptable derivative thereof is released;
after 4 hours 30–60% of the propranolol or a pharmaceutically acceptable derivative thereof is released;
after 8 hours 50–80% of the propranolol or a pharmaceutically acceptable derivative thereof is released;
not less than 70% of the propranolol or a pharmaceutically acceptable derivative thereof is released after 12 hours; and
not less than 85% of the propranolol or a pharmaceutically acceptable derivative thereof is released after 20 hours.

6. The controlled release pharmaceutical dosage form as defined in claim 5 that exhibits the following dissolution profile when tested in a USP type II apparatus at 75 rpm in 900 ml of simulated gastric fluid and at 37° C.:
after 2 hours 15–30% of the propranolol or a pharmaceutically acceptable derivative thereof is released;
after 4 hours 45–60% of the propranolol or a pharmaceutically acceptable derivative thereof is released;
not less than 60% of the propranolol or a pharmaceutically acceptable derivative thereof is released after 8 hours;
not less than 75% of the propranolol or a pharmaceutically acceptable derivative thereof is released after 12 hours; and
not less than 90% of the propranolol or a pharmaceutically acceptable derivative thereof is released after 20 hours.

7. The controlled release pharmaceutical dosage form as defined in claim 5 wherein the core consists essentially of:
30–70% propranolol or a pharmaceutically acceptable derivative thereof;
10–40% microcrystalline cellulose;
1–15% ethylcellulose;
10–35% sugar sphere, wherein the foregoing percentages are based on the total weight of the core; and the coating consists essentially of:
50–90% ethylcellulose;
acetyl tributyl citrate;
1–20% hydroxypropyl methylcellulose; and talc, wherein the foregoing percentages are based on the total weight of the coating.

8. The controlled release pharmaceutical dosage form as defined in claim 5 wherein the core consists essentially of:
50–60% propranolol or a pharmaceutically acceptable derivative thereof;
20–30% microcrystalline cellulose;
3–10% ethylcellulose; and
15–30% inert pellet starting material; and the coating consists essentially of:
60–80% ethylcellulose;
5–10% acetyl tributyl citrate;
5–15% hydroxypropyl methylcellulose; and
5–15% of talc.

* * * * *